US00PP17440P2

(12) United States Plant Patent
Westhoff

(10) Patent No.: US PP17,440 P2
(45) Date of Patent: Feb. 20, 2007

(54) ***ARGYRANTHEMUM* PLANT NAMED 'WESARWHI'**

(50) Latin Name: *Argyranthemum frutescens*
Varietal Denomination: Wesarwhi

(75) Inventor: Heinrich Westhoff, Südlohn (DE)

(73) Assignee: J. + H. Westhoff Interpel, Südlohn (DE)

( * ) Notice: Subject to any disclaimer, the term of this patent is extended or adjusted under 35 U.S.C. 154(b) by 45 days.

(21) Appl. No.: 11/146,208

(22) Filed: Jun. 6, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP15,426 P2 * 12/2004 Brown ..... Plt./263

OTHER PUBLICATIONS

UPOV ROM GTITM Computer Database, GTI Jouve Retrieval Software 2006/05 Citation for 'Wesarwhi'.*

* cited by examiner

*Primary Examiner*—Wendy Haas
(74) *Attorney, Agent, or Firm*—C. A. Whealy

(57) ABSTRACT

A new and distinct cultivar of *Argyranthemum* plant named 'Wesarwhi', characterized by its compact, upright and mounded plant habit; vigorous growth habit; freely branching habit; dense and bushy plant habit; relatively large and broad leaves; freely flowering habit with numerous inflorescences per plant; and daisy-type inflorescences with white-colored ray florets and gold yellow-colored disc florets.

1 Drawing Sheet

Botanical designation: *Argyranthemum frutescens.*
Cultivar denomination: 'Wesarwhi'.

BACKGROUND OF THE INVENTION

The present invention relates to a new and distinct cultivar of *Argyranthemum* plant, botanically known as *Argyranthemum frutescens* and hereinafter referred to by the cultivar name 'Wesarwhi'.

The new *Argyranthemum* is a product of a planned breeding program conducted by the Inventor in Südlohn, Germany. The objective of the breeding program is to develop new vigorous and freely flowering *Argyranthemum* cultivars with attractive and unique inflorescence coloration.

The new *Argyranthemum* originated from a cross-pollination made by the Inventor of a proprietary selection of *Argyranthemum* identified as code number 02P20, not patented, as the female, or seed, parent with a proprietary selection of *Argyranthemum* identified as code number 02P10, not patented, as the male, or pollen, parent. The new *Argyranthemum* was discovered and selected in 2003 by the Inventor in a controlled environment in Südlohn, Germany as a single plant within the resulting progeny from the cross-pollination.

Asexual reproduction of the new cultivar by terminal cuttings at Südlohn, Germany since 2003, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Wesarwhi' and distinguish the new *Argyranthemum* as a new and distinct cultivar:

1. Compact, upright and mounded plant habit.
2. Vigorous growth habit.
3. Freely branching habit; dense and bushy plant habit.
4. Relatively large and broad leaves.
5. Freely flowering habit with numerous inflorescences per plant.
6. Daisy-type inflorescences with white-colored ray florets and golden yellow-colored disc florets.

Plants of the new *Argyranthemum* differ from plants of the female parent selection in the following characteristics:

1. Plants of the new *Argyranthemum* are more compact than plants of the female parent selection.
2. Leaves of plants of the new *Argyranthemum* are broader than leaves of plants of the female parent selection.
3. Plants of the new *Argyranthemum* are more freely flowering than plants of the female parent selection.
4. Plants of the new *Argyranthemum* have larger inflorescences than plants of the female parent selection.

Plants of the new *Argyranthemum* differ from plants of the male parent selection in the following characteristics:

1. Plants of the new *Argyranthemum* are more freely branching than plants of the male parent selection.
2. Plants of the new *Argyranthemum* have larger inflorescences than plants of the male parent selection.
3. Ray florets of plants of the new *Argyranthemum* are white in color whereas ray florets of plants of the male parent selection are creamy white in color.

Plants of the new *Argyranthemum* can be compared to plants of the cultivar Dana, not patented. In side-by-side comparisons conducted in Südlohn, Germany, plants of the new *Argyranthemum* differed from plants of the cultivar Dana in the following characteristics:

1. Plants of the new *Argyranthemum* had much shorter internodes and were more compact than plants of the cultivar Dana.
2. Leaves of plants of the new *Argyranthemum* were much larger, much broader and more green in color than leaves of plants of the cultivar Dana.
3. Ray florets of plants of the new *Argyranthemum* were broader than ray florets of plants of the cultivar Dana.

BRIEF DESCRIPTION OF THE PHOTOGRAPHS

The accompanying colored photographs illustrated the overall appearance of the new cultivar, showing the colors as true as it is reasonably possible to obtain in colored reproductions of this type. Colors in the photographs may differ slightly from the color values cited in the detailed botanical description which accurately describe the colors of the new *Argyranthemum*.

The photograph at the top of the sheet comprises a side perspective view of a typical flowering plant of 'Wesarwhi' grown in a container.

The photograph at the bottom of the sheet comprises a close-up view of a typical inflorescence of 'Wesarwhi'.

DETAILED BOTANICAL DESCRIPTION

The aforementioned photographs, following observations and averaged measurements describe plants grown in Südlohn, Germany in a glass-covered greenhouse during the spring and summer. During the production of the plants, day temperatures ranged from 20° C. to 25° C., night temperatures ranged from 16° C. to 18° C. and light levels ranging from 3,000 to 50,000 lux. Plants were pinched one time. Plants had been growing for about 40 weeks when the photographs and description were taken. Color references are made to The Royal Horticultural Society Colour Chart, 2001 Edition, except where general terms of ordinary dictionary significance are used.

Botanical classification: *Argyranthemum frutescens* cultivar Wesarwhi.

Parentage:

*Female parent.*—Proprietary selection of *Argyranthemum frutescens* identified as 02P20, not patented.

*Male parent.*—Proprietary selection of *Argyranthemum frutescens* identified as 02P10, not patented.

Propagation:

*Type.*—Terminal vegetative cuttings.

*Time to initiate roots, summer.*—About 7 to 10 days at 18° C. to 20° C.

*Time to initiate roots, winter.*—About 10 to 14 days at 18° C. to 20° C.

*Time to produce a rooted young plant, summer.*—About 15 to 20 days at 18° C. to 20° C.

*Time to produce a rooted young plant, winter.*—About 18 to 21 days at 18° C. to 20° C.

*Root description.*—Fibrous, fine; white in color.

*Rooting description.*—Freely branching; dense.

Plant description:

*General appearance.*—Inverted triangle; compact, upright and mounded plant form with dense foliage and inflorescences held above and beyond the foliage; plants becoming nearly spherical with development. Vigorous growth habit.

*Plant height.*—About 42 cm.

*Plant width.*—About 60 cm.

*Lateral branch description.*—Quantity per plant: About three primary lateral branches, each with about eight secondary lateral branches. Length: About 29.5 cm. Diameter: About 4.6 mm. Internode length: About 4.6 mm. Aspect: Initially upright to outwardly spreading. Texture, young branches: Smooth, glabrous. Texture, mature branches: Woody. Strength: Strong; young branches, flexible. Color, young branches: 146C. Color, mature branches: N199A.

*Foliage description.*—Arrangement: Alternate, simple. Length: Large, about 9.4 cm. Width: Broad, about 4.4 cm. Shape: Pinnatifid, deeply dissected. Apex: Acute. Base: Attenuate. Margin: Entire; deeply and finely dissected. Texture, upper and lower surfaces: Very slightly pubescent. Venation pattern: Pinnate. Petiole length: About 3 cm. Petiole diameter: About 2.7 mm. Petiole texture, upper and lower surfaces: Slightly pubescent. Color: Developing foliage, upper and lower surfaces: 144A. Fully expanded foliage, upper surface: 137A to 137B; venation, 137C. Fully expanded foliage, lower surface: 137C; venation, 137C. Petiole, upper surface: 137C. Petiole, lower surface: 144A.

Inflorescence description:

*Appearance.*—Daisy-type inflorescences with broadly ligulate ray florets. Disc and ray florets develop acropetally on a capitulum. Inflorescences held upright and outwardly on terminal and axillary peduncles. Inflorescences positioned perpendicular to the peduncles. Inflorescences persistent.

*Flowering response.*—Under natural conditions, plants flower from spring to early fall in Germany; plants flower continuously during this period.

*Inflorescence longevity.*—Inflorescences last about one week on the plant.

*Quantity of inflorescences.*—Freely flowering, about five open inflorescences and inflorescence buds per lateral branch.

*Fragrance.*—None detected.

*Inflorescence size.*—Diameter: About 3.3 cm. Depth (height): About 8 mm. Diameter of disc: About 1 cm. Receptacle height: About 4.6 mm. Receptacle diameter: About 8.6 mm.

*Inflorescence buds.*—Height: About 4 mm. Diameter: About 5 mm. Shape: Oblate. Color: Towards the apex, 138A to 138B; towards the base, 199A to 199C.

*Ray florets.*—Quantity per inflorescence: About 13 to 15 arranged in a single whorl. Shape: Broadly ligulate. Length: About 1.5 cm. Width: About 5.6 mm. Apex: Obtuse; slightly emarginate. Base: Obtuse. Margin: Entire. Texture, upper and lower surfaces: Smooth, glabrous; satiny. Aspect: Initially upright; with development, horizontal to the peduncle; eventually reflexing. Color: When opening, upper and lower surfaces: Brighter than 155C. Fully opened, upper and lower surfaces: Brighter than 155C.

*Disc florets.*—Arrangement: Massed at the center of the inflorescence. Quantity per inflorescence: About 80. Shape: Tubular, elongated; apex, five-pointed; base, fused. Length: About 5 mm. Diameter, apex: About 2.4 mm. Diameter, base: Less than 1 mm. Color: Immature: 15A. Mature, apex: 14B. Mature, mid-section: 145C. Mature, base: 145D.

*Involucral bracts* (*phyllaries*).—Appearance: Scale-like; margins, papery. Quantity per inflorescence: About 14 to 18; imbricate. Length: About 4.7 mm. Width: About 3.1 mm. Shape: Elliptic. Apex: Acute. Base: Truncate. Margin: Entire. Texture, upper and lower surfaces: Smooth, glabrous. Color, upper surface: 144A to 144B; towards the margin, 199A to 199D. Color, lower surface: 145B to 145C; towards the margin, 199D.

*Peduncle.*—Strength: Moderately strong; wiry. Aspect: Upright to about 45° from vertical. Length, terminal inflorescence: About 4.3 cm. Length, fourth inflorescence: About 4.5 cm. Diameter: About 1 mm. Texture: Slightly pubescent. Strength: Strong, flexible. Color: 144A.

*Reproductive organs.*—Androecium: Only on disc florets. Stamen quantity per floret: Five. Anther size: Less than 1 mm. Anther shape: Ovoid. Anther color: 15A. Amount of pollen: Scarce. Pollen color: 15A. Gynoecium: Present on ray and disc florets. Pistil quantity per floret: One. Pistil length: About 5.5 mm. Stigma shape: Two-parted. Stigma color: 15A. Style length: About 3.2 mm. Style color: 154D. Ovary color: 145D.

*Seed/fruit.*—Seed and fruit production has not been observed.

Disease/pest resistance: Resistance to pathogens and pests common to *Argyranthemums* has not been observed on plants grown under commercial conditions Temperature/weather tolerance: Plants of the new *Argyranthemum* have been observed to be tolerant to rain, wind and to temperatures from 5° C. to 30° C.

It is claimed:

1. A new and distinct cultivar of *Argyranthemum* plant named 'Wesarwhi', as illustrated and described.

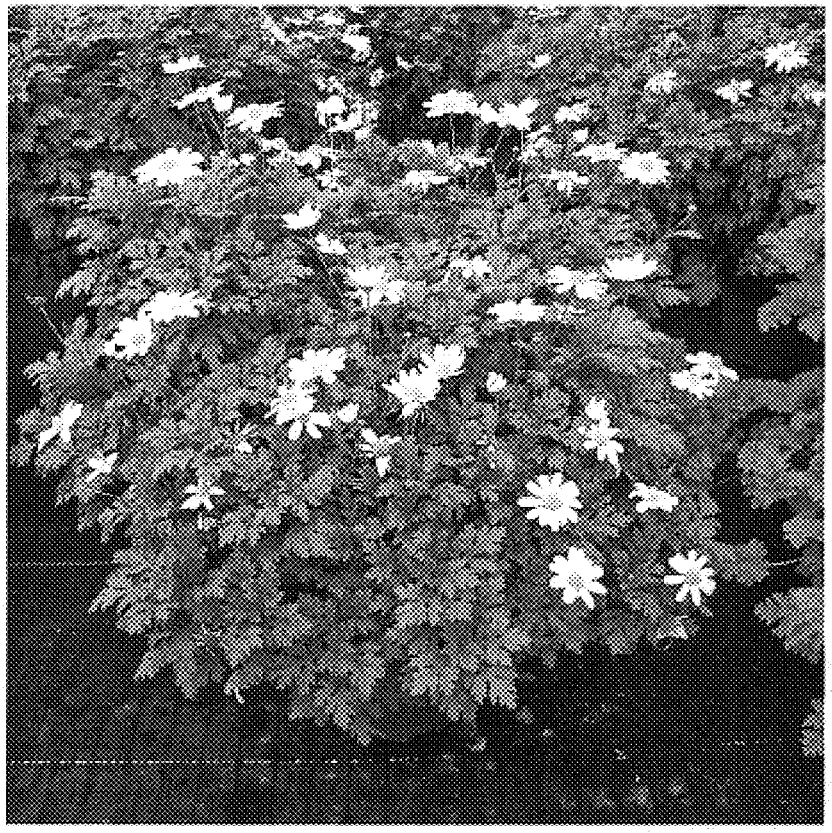
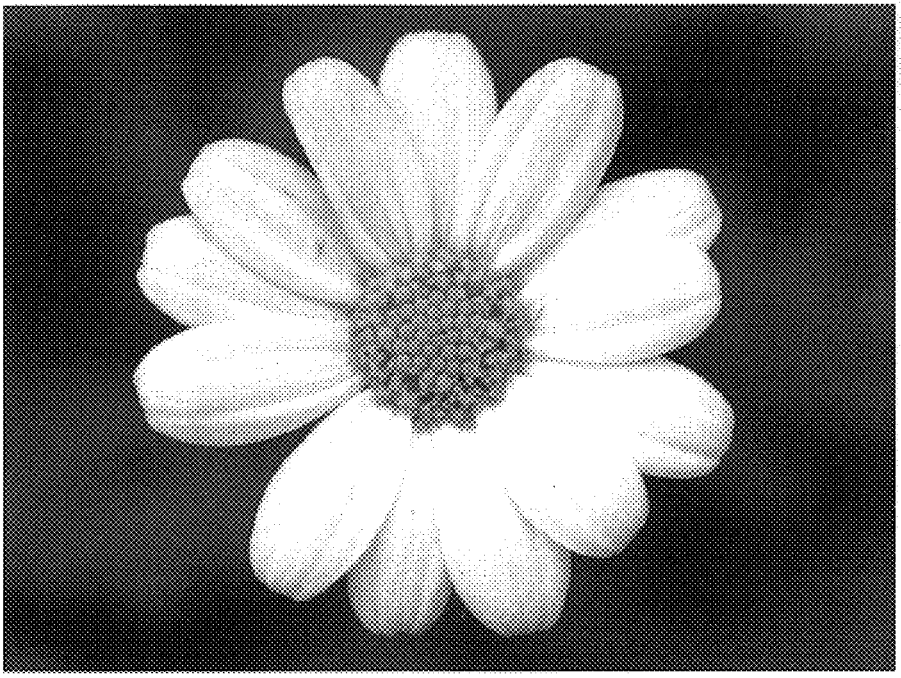

* * * * *